United States Patent [19]

Kaufhold et al.

[11] 4,320,237

[45] Mar. 16, 1982

[54] PROCESS FOR THE HYDROFORMYLATION OF OLEFINS

[75] Inventors: Manfred Kaufhold, Marl; Johann Gaube, Rössdorf, both of Fed. Rep. of Germany

[73] Assignee: Chemische Werke Hüls AG, Marl, Fed. Rep. of Germany

[21] Appl. No.: 894,325

[22] Filed: Apr. 7, 1978

Related U.S. Application Data

[62] Division of Ser. No. 711,460, Aug. 4, 1976, abandoned.

[30] Foreign Application Priority Data

Aug. 27, 1975 [DE] Fed. Rep. of Germany ....... 2538037

[51] Int. Cl.³ .............................................. C07C 27/22
[52] U.S. Cl. .................................... 568/909; 422/189; 422/224
[58] Field of Search ......................................... 568/909

[56] References Cited

U.S. PATENT DOCUMENTS

| | | | |
|---|---|---|---|
| 3,113,974 | 12/1963 | Heimsch et al. | 568/909 |
| 3,220,998 | 11/1965 | Berger | 23/285 |
| 3,567,396 | 3/1971 | Setzler, Jr. | 23/285 |
| 3,759,669 | 9/1973 | Aaron et al. | 23/283 |

Primary Examiner—Joseph E. Evans
Attorney, Agent, or Firm—Wells & Wells

[57] ABSTRACT

Method for the hydroformylation of olefins with carbon monoxide and hydrogen in the presence of soluble cobalt compounds as the catalyst at an elevated temperature and under increased pressure, and optionally in the presence of paraffins and/or other inert diluents. The hydroformylation is conducted, in a first stage, up to a conversion of about 40-75 percent with remixing of the reaction mixture, and then, in a second stage, up to a conversion of at least 95 percent, preferably 95-98 percent, without remixing.

15 Claims, 1 Drawing Figure

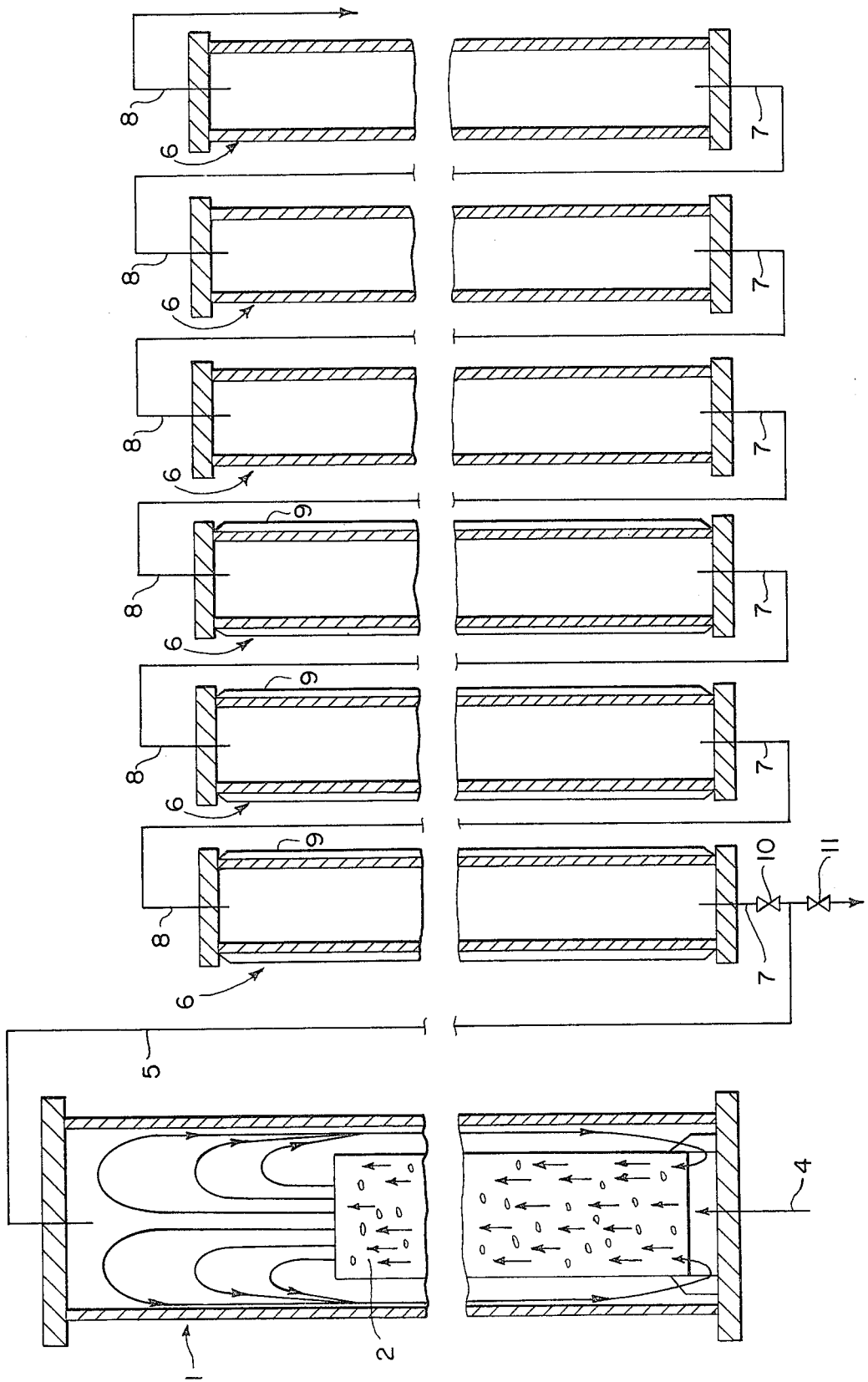

PROCESS FOR THE HYDROFORMYLATION OF OLEFINS

This is a division of application Ser. No. 711,460, filed Aug. 4, 1976, now abandoned.

CROSS REFERENCES TO RELATED APPLICATIONS

Applicants claim priority under 35 U.S.C. 119 for application Ser. No. P 25 38 037.4-42, filed Aug. 27, 1975, in the Patent Office of the Federal Republic of Germany.

The disclosure of copending application Ser. No. 566,523, filed Apr. 8, 1975, now U.S. Pat. No. 4,061,687, is incorporated herein to show the state of the art of cobalt catalysts useful in the present invention.

BACKGROUND OF THE INVENTION

The present invention relates to a method for the hydroformylation of olefins by reaction with carbon monoxide and hydrogen in the presence of soluble cobalt compounds at an elevated temperature under increased pressure, producing the corresponding alcohols which contain one more carbon atom.

The state of the prior art of the oxo process and of cobalt catalysts used therein may be ascertained by reference to the Kirk-Othmer "Encyclopedia of Chemical Technology", Vol. 14 (1967) under the section "Oxo Process", on pages 373–390, particularly pages 375–376, which disclose the cobalt catalysts, and pages 383–384, which disclose the catalyst removal and recovery, and U.S. Pat. Nos. 2,767,048, 2,816,933 and 2,841,617 of Joseph K. Mertzweiller, which issued Oct. 16, 1956, Dec. 17, 1957 and July 1, 1958, respectively.

In the hydroformylation of olefins with carbon monoxide and hydrogen according to the oxo process, high conversion rates are desirable, because unreacted olefins are converted into less valuable paraffins during the hydrogenation necessary during the course of the usual working-up procedure.

Although high conversion rates can be forcibly obtained even in case of sluggishly reacting olefins by means of high catalyst concentrations, these favor, on the other hand, the formation of undesirable higher boiling by-products and thereby impair the alcohol yield. An increase in the temperature and an extension of the residence time have a similarly adverse effect on the yield. The latter furthermore reduces the space time yield and thus is a burden on the economy of the process.

Propene can be reacted, due to its high reaction velocity, with CO and $H_2$ with satisfactory space time yields at a residence time of 1–2 hours (J. Falbe, Ullmanns Encylkopaedie der technischen Chemie (Ullmann's Encyclopedia of Technical Chemistry) 3rd Ed., 1970, Supplemental Volume, p. 90). The reaction velocity of the olefins decreases with an increasing chain length and with an increasing degree of branching (J. Falbe, "Synthesen mit Kohlenmonoxid" (Synthesis with Carbon Monoxide), Springer publishers, 1967, p. 29). Although it is still economical to subject higher α-olefins to hydroformylation by means of the heretofore known reaction conditions and reactors, this becomes impossible for higher olefins having an internally positioned double bond and for olefins having branched carbon chains wherein the reaction velocity is only ⅓ of the reaction speed of α-olefins having the same chain length (J. Falbe, loc. cit.).

SUMMARY OF THE INVENTION

Having in mind the limitations of the prior art, it is an object of the present invention to subject to hydroformylation even slowly reacting olefins with conversion rates of at least 95 percent and with a yield of the corresponding alcohols of about 80 percent.

This object is achieved by conducting the hydroformylation of olefins in a first stage up to a conversion of about 40–75 percent with a remixing of the reaction mixture, and then in a second stage to a conversion of at least 95 percent without remixing.

BRIEF DESCRIPTION OF THE DRAWING

An apparatus for the hydroformylation of olefins with carbon monoxide and hydrogen in the presence of cobalt compounds at elevated temperatures under increased pressures in two stages is illustrated in the FIGURE. This apparatus consists of the pressure-proof back mix reactor 1 having preferably a ratio of internal diameter to its length of 1:5 to 1:25, especially 1:8 to 1:20, with the guide tube 2 arranged centrally in the interior and being open at the bottom and at the top, with the feed nozzle for the reaction mixture 4 provided at the bottom, and with the discharge means 5 arranged at the top, as well as a plurality of subsequently connected, pressure-proof tubular reactors 6. These reactors 6 preferably have a ratio of internal diameter to length of 1:20 to 1:1000, especially 1:25 to 1:500, with the inlet nozzles 7 arranged at the bottom and the discharge conduits 8 arranged at the top. Only the first few of the tubular reactors 6 require cooling jackets 9. The valves 10 and 11 are illustrated in the drawing merely as examples. During operation, valve 10 is opened and valve 11 is closed. To withdraw samples from the reaction mixture of the first stage, 10 is closed and 11 is opened.

DESCRIPTION OF THE PREFERRED EMBODIMENTS

Olefins suitable in the present invention include the following: straight-chain α-olefins of 6–10 carbon atoms, such as 1-hexene, 1-heptene, 1-octene, 1-nonene, and 1-decene, advantageous for the production of plasticizers, as well as α-olefins of 10–20 carbon atoms, such as 1-decene, 1-undecene, 1-dodecene, 1-tridecene, 1-tetradecene, 1-pentadecene, 1-hexadecene, 1-heptadecene, 1-octadecene, 1-nonadecene, 1-eicosene, and higher α-olefins, which are suited for the manufacture of detergents.

These olefins are subjected to hydroformylation at a relatively low temperature. The hydroformylation is used with particular advantage with olefins which lead themselves otherwise to hydroformylation only with difficulties, such as those with 6–20 carbon atoms and internally positioned double bonds, e.g. n-hexene-2 or -3, n-heptene-2 or -3 or -4, n-octene-2 or -3 or -4, n-nonene-2 or -3 or -4 or -5, 2- or 3- or 4or 5-decene, 2- or -3 or 4- or 5- or 6-undecene, 2- or 3- or 4- or 5- or 6-dodecene, 2- or 3- or 4- or 5- or 6- or 7-tridecene, 2- or 3- or 4- or 5- or 6- or 7-tetradecene, and the corresponding higher olefins, as well as branched olefins, such as dimerized propene, heptenes made from propene and butenes, octenes produced by the dimerization of butenes, known as diisobutylene, codibutylene, nonenes prepared by trimerization of propene, so-called tripropylene, and higher condensed olefins, as well a β-branched α-olefins, such as for example, isobutylene, 2-ethyl-1-hexene, etc.

All of the olefins are used individually, in a mixture with one another, and/or diluted with paraffins and/or other inert diluents, such as alcohols, ethers, aromatic hydrocarbons, cycloaliphatics, etc.

As the catalyst, cobalt compounds soluble in the reaction mixture are conventionally employed, especially cobalt carbonyls or cobalt hydrocarbonyls, dissolved in the olefin used or in a solvent such as, for instance, isobutanol or other alcohols, especially oxo alcohols formed during the reaction or high-boiling by-products, as well as paraffins, aromatic hydrocarbons, cycloaliphatic hydrocarbons, ethers, etc., in an amount so that a concentration of about 0.01–2.0 percent by weight, preferably about 0.05–0.5 percent by weight, is present in the reaction mixture.

The source of carbon monoxide and hydrogen is customarily synthesis gas with 70–30 percent carbon monoxide and 30–70 percent hydrogen, preferably about 45 percent carbon monoxide and 55 percent hydrogen, which is used at a pressure of 200–350 bars, preferably 280–300 bars. The quantity of CO and $H_2$ is approximately the 5- to 1.2-fold molar amount, based on the olefin employed. The reaction temperature is 100°–200° C. and during the hydroformylation of α-olefins, this temperature is advantageously 100°–130° C. and during the hydroformylation of olefins having internally positioned double bonds and/or with chain branches preferably 160°–180° C. If necessary, the heat of reaction is removed by cooling the reactors. The starting materials, namely olefins, optionally paraffins or other inert diluents, cobalt compounds, carbon monoxide, and hydrogen, the latter suitably in the form of synthesis gas, are used in the cold state, i.e., without preheating. After the reaction has been accomplished, the reaction mixture which contains—in addition to unreacted olefin, optionally paraffins and diluents and the cobalt catalyst—primarily aldehydes and alcohols with a carbon chain longer by one carbon atom than the olefins and minor amounts of higher boiling residues is conventionally freed of cobalt and then subjected to a hydrogenation to convert the sensitive aldehydes into the corresponding alcohols. The reaction product is then worked up by distillation.

The first stage of the reaction with remixing is conducted in a back mix reactor. The remixing step is advantageously effected by introducing the starting substances in conjunction with a guide tube in the interior of the reactor (jet pump action, gas agitation).

The reaction is carried out, for example by adjusting the reactor size or by setting a suitable reaction temperature, up to a conversion of 40–75 percent, preferably 50–60 percent. For reasons of economy, the step should not be conducted at a conversion of below 40 percent. Above a conversion of 75 percent in the first stage, the yield of alcohols begins to become impaired.

In the second stage, the hydroformylation is completed, while avoiding any remixing, up to a conversion of 95–98 percent, based on the olefins. If the conversion is increased beyond 98 percent, the undesirable higher boiling by-products are increased, while the yield of alcohols is impaired. A remixing is avoided by conducting the second stage of the hydroformylation in a sufficiently long and thin tube connected to the back mix reactor. The volume of the tubular reactor of the second stage is suitably 5 to 1.2 times the volume of the back mix reactor. Since a single tube would have to be impractically long in certain cases, a plurality of 2–100, preferably 4–30 slim, upright tubes is used with special advantage and the reaction mixture flows successively through these tubes, the feed being accomplished in each case from the bottom by means of a nozzle, while the mixture is in each case discharged at the top. Only the initial ones of the plurality of upright, slim tubes require cooling, suitably by means of a cooling jacket traversed by a cooling medium.

It is possible according to the method of the present invention to subject to hydroformylation, with an advantage that could not be foreseen, longer chain olefins and especially olefins of 6–20 carbon atoms and with an internally positioned double bond and/or with branched carbon chains, with conversions of more than 95 percent with a residence time reduced to approximately half the time required by a mixing reactor (state of the art), thus obtaining maximum yields of alcohols.

The back mix reactor 1 shown in the drawing and used in the following Examples 1–4 is well known in the art see Perry, Chemical Engineers (Handbook, 5th Ed. (1973). chapter 4, pp 21 to 24, chapter 6, pp 14 to 15 and chapter 19. pp 8 to 12).

In the Examples 2 and 3, the following process variables are used:

| | |
|---|---|
| volume tubular reactor to volume back mix reactor | 3:1 and 1.5:1 |
| back mix reactor olefin conversion rate | 55 and 71% |
| whole system olefin conversion rate | 97.1 and 97.8% |
| residence time back mix reactor | 0.0795 and 0.159 hours |
| residence time whole system | 0.33 and 0.40 hours |
| temperature in back mix reactor | 100 to 200° C. |
| pressure in whole system | 280 to 300 bars |
| concentration of cobalt catalyst based on weight of cobalt | 0.1 weight % |
| input volume of olefin-paraffin mixture | 40 liters per hour |

EXAMPLE 1

Comparative Example

A back mix reactor constituted by a vertically disposed high pressure pipe having an internal diameter of 108 mm, a length of 1000 mm, and an effective volume of 8.17 liters, comprising a guide tube centrally arranged in the interior at 100 mm above the bottom having an inner diameter of 55 mm and a length of 500 mm, is charged through a nozzle arranged centrally in the bottom continuously with 12 liters per hour of an olefin-paraffin mixture consisting of 72 percent $C_{10}$- to $C_{11}$-n-paraffins and 28 percent n-olefins having centrally positioned double bonds (among these about 8 percent $C_{10}$- and 92 percent $C_{11}$-olefin). The reaction mixture is maintained at a temperature of 170° C. and under a pressure of 280 bars. Simultaneously, synthesis gas with 45 percent by volume of CO and 55 percent by volume of $H_2$ is introduced through the same nozzle in an amount to form a quantity of waste gas of 3 $Nm^3$ per hour. Likewise through the same nozzle and at the same time, 4 liters per hour of a solution of cobalt hydrocarbonyl in isobutanol is added in such a quantity that the content of metallic cobalt in the reactor is approximately 0.1 percent by weight.

The reaction product is withdrawn via a short dip pipe mounted in the head of the back mix reactor; freed of cobalt in a conventional manner with air in the presence of aqueous formic acid; washed with water; hydrogenated over a copper chromite catalyst, and then separated into the components by distillation. The olefin conversion is 89.6 percent, the residence time is 0.68 hour. 100 moles of reacted olefin results in 76.6 moles of alcohol, 16.3 moles of paraffines, and 7.0 moles of higher boiling residues. This corresponds to an alcohol yield, based on the utilized olefin, of 68.7 percent.

EXAMPLE 2

An apparatus is employed as illustrated in the drawing. The back mix reactor 1 has an internal diameter of 80 mm and a length of 640 mm. The reactor is furnished with a guide tube 2 having a diameter of 44 mm and a length of 320 mm, mounted centrally 50 mm above the bottom. The subsequently connected tubular reactor 6 is subdivided into six slim, upright high pressure tubes having a diameter of 45 mm and respectively a length of 1000 mm, in communication with one another and with the back mix reactor by means of pipes having an internal diameter of 10 mm. All of the reactors comprise centrally in the bottom a nozzle for the introduction of the reaction mixture and centrally in the head of short dip pipe for discharge purposes. The effective volume of the back mix reactor is 3.18 liters, the effective volume of the tubular reactors is 9.54 liters, and that of the connecting conduits is 0.5 liter, so that a total volume of the apparatus results amounting to 13.22 liters. After heating the system to 170° C. and adjusting a synthesis gas pressure of 280 bars, 40 liters per hour of the olefin-paraffin mixture which has also been used in Example 1 and contains 28 percent internally positioned n-olefins is continuously introduced, along with 10 liters of isobutanol with such an amount of dissolved cobalt hydrocarbonyl that the content of metallic cobalt in the reaction mixture is 0.1 percent by weight, and finally such a quantity of synthesis gas (with 45 percent by volume of CO and 55 percent by volume of $H_2$) that an amount of waste gas of 4 $Nm^3$ per hour is obtained. The temperature of the reaction mixture is maintained at 170° C. in the back mix reactor and in the subsequently connected reaction tubes. In between, a sample is withdrawn by closing the valve 10 and opening the valve 11, yielding after having been worked up as set forth in Example 1 an olefin conversion of 55 percent at the outlet of the back mix reactor. When the reaction product exists from the system after passing entirely therethrough, a conversion is determined of 97.1 percent. The residence time is merely 0.33 hour. 100 moles of reacted olefin results, after conducting the usual working up operation according to Example 1, in 82.4 moles of alcohol, 12.4 moles of paraffins, and 5.2 moles of higher boiling residues. This corresponds to an alcohol yield, based on the olefin utilized, of 80.0 percent. A comparison with Example 1 shows that, by using the mode of operation according to the present invention, with a substantially shorter residence time and thereby with a higher space time yield, one attains a higher conversion of the olefins and a better yield of alcohols, with the formation of undesired paraffins and higher boiling residues being suppresed.

EXAMPLE 3

An apparatus is utilized as shown in the drawing and corresponding to Example 2; also, the same reaction conditions are employed, except that the back mix reactor has an internal diameter of 80 mm, a length of 1300 mm, and an effective volume of 6.36 liters, so that the total volume of the arrangement is 16.40 liters. If, according to Example 2, 40 liters of the olefin-paraffin mixture per hour is continuously introduced, along with 10 liters of a solution of cobalt hydrocarbonyl in isobutanol and synthesis gas in a quantity so that 4 $Nm^3$ of waste gas is produced, then an olefin conversion is obtained at the outlet of the back mix reactor of 71.0 percent and, after traversing the entire system, the olefin conversion rate attained is 97.8 percent. The residence time is 0.40 hour. 100 moles of reacted olefin results, after conducting the usual working-up steps in accordance with Example 1, in 81.2 moles of alcohol, 13.2 moles of paraffins, and 5.6 moles of high boiling residues. This corresponds to an alcohol yield, based on the olefin utilized, of 79.6 percent. A comparison with Example 2 demonstrates that, with a conversion in the back mix reactor of 71 percent and, at the point where the reaction mixture leaves the entire system, of 97.8 percent, the yield of alcohols is practically not impaired at all.

EXAMPLE 4

Comparative Example

The apparatus of Example 3 is utilized, along with the same reaction conditions, with the difference that in order to get another olefin conversion in the back mix reactor continuously only 10 liters of the olefin-paraffin mixture with 28 percent internally positioned n-olefins is introduced per hour, along with 2.5 liters of the solution of cobalt hydrocarbonyl in isobutanol. At the outlet of the back mix reactor, the olefin conversion is 83.0 percent, and the conversion at the outlet from the entire system is 99.1 percent. The residence time is 1.64 hours. 100 moles of reacted olefin results in 77.0 moles of alcohol, 12.6 moles of paraffins, and 10.4 moles of high boiling residues. This corresponds to an alcohol yield, based on the olefin used, of 76.3 percent.

A comparison with Examples 2 and 3 clearly demonstrates that, with a conversion at the outlet of the back mix reactor of 83 percent and of 99.1 percent when leaving the entire system, the yield of alcohols is substantially impaired, while the formation of undesirable paraffins and high boiling residues is increased.

We claim:

1. In the process for the hydroformylation of olefins with carbon monoxide and hydrogen in the presence of soluble cobalt compounds as a catalyst at an elevated temperature and under increased pressure, the improvement comprising conducting said hydroformylation in a first stage with remixing of a reaction mixture comprising said olefins, carbon monoxide and hydrogen for a first period of time sufficient to produce an olefin conversion of about 40-75 percent as a converted product and then in a second stage continuing said hydroformylation of said converted product without remixing for a second period of time sufficient to produce an olefin conversion of about 95-98 percent, said olefins having 6 or more carbon atoms and selected from the group consisting of alpha olefins, olefins having internally positioned double bonds, olefins with branches in the carbon chain, olefins having branches in the carbon chain and internally positioned double bonds and mixtures of said olefins.

2. The method of claim 1, wherein said first stage is carried out in a pressure-proof back mix reactor (1) with a guide tube (2) arranged centrally in the interior and being open at the bottom and at the top, with a feed nozzle for the reaction mixture (4) disposed at the bottom, as well as with a discharge means (5) arranged at the top, said back mix reactor having a ratio of internal diameter to length of 1:5 to 1:25, and said second stage is carried out in a plurality of subsequently connected, pressure-proof tubular reactors (6) with inlet nozzles (7) arranged at the bottom and discharge conduits (8) arranged at the top, said plurality of subsequently connected tubular reactors (6) having a ratio of internal diameter to length of 1:20 to 1:1000, and wherein the total volume of said plurality of tubular reactors is 5 to 1.2 times the volume of said back mix reactor.

3. The method of claim 2, wherein said tubular reactors have cooling jackets (9).

4. The method of claim 2, wherein the first, second and third of said tubular reactors have cooling jackets.

5. The method of claim 1, wherein said carbon monoxide and hydrogen comprise synthesis gas in a concentration of 70–30 percent carbon monoxide and 30–70 percent hydrogen, said synthesis gas comprising 5 to 1.2 fold molar amount based on said olefins.

6. The method of claim 5, wherein said hydroformylation is carried out at a temperature of about 100°–200° C.

7. The method of claim 1, wherein said olefins are α-olefins having 6–10 carbon atoms, and said hydroformylation is carried out at a temperature of about 100°–130° C.

8. The method of claim 1, wherein said olefins have 6–20 carbon atoms and said hydroformylation is carried out at a temperature of about 160°–180° C.

9. The method of claim 6, wherein said hydroformylation is carried out at a pressure of about 200–350 bars.

10. The method of claim 1, wherein said first stage is carried out in a back mix reactor and said second stage is carried out in tubular reactors and the volume of said tubular reactors to the volume of said back mix reactor is between 3:1 and 1.5:1.

11. The method of claim 10, wherein said first stage has an olefin conversion rate of 55–71%.

12. The method of claim 11, wherein said first and second stage have an olefin conversion rate of 97.1–97.8%.

13. The method of claim 10, wherein said back mix reactor has a residence time of 0.0795–0.159 hours.

14. The method of claim 13, wherein said back mix reactor and said tubular reactors have a total residence time of 0.33–0.40 hours.

15. The method of claim 9, wherein the input of olefins is 40 liters per hour.

* * * * *